United States Patent [19]  
Terayama

[11] 4,257,420  
[45] Mar. 24, 1981

[54] RING APPLICATOR WITH AN ENDOSCOPE
[75] Inventor: Toshiki Terayama, Kodaira, Japan
[73] Assignee: Olympus Optical Co., Ltd., Tokyo, Japan
[21] Appl. No.: 41,339
[22] Filed: May 22, 1979
[51] Int. Cl.³ ............... A61B 17/12; A61B 1/00
[52] U.S. Cl. ........................ 128/303 A; 128/4; 128/326
[58] Field of Search .................. 128/3–8, 128/303 A, 326, 320, 321, 325, 328

[56] References Cited  
U.S. PATENT DOCUMENTS

| 3,870,048 | 3/1975 | Yoon | 128/6 |
| 3,911,923 | 10/1975 | Yoon | 128/303 A |
| 3,924,608 | 12/1975 | Mitsui | 128/6 X |
| 4,085,743 | 4/1978 | Yoon | 128/303 A X |

Primary Examiner—Robert W. Michell  
Assistant Examiner—Michael H. Thaler

[57] ABSTRACT

A ring applicator with an endoscope comprises an outer tube, an inner tube reciprocatingly inserted into the outer tube and having a rubber ring removably mounted on the inner tube, and an endoscope reciprocatingly inserted into the inner tube. An open type forceps is reciprocatingly inserted into a channel of the endoscope. The applicator further comprises an operation device which is movable toward the proximal end of an operation unit connected to the outer tube, thereby pulling the forceps into the inner tube to close the forceps, then pulling both the forceps and the endoscope into the inner tube, and finally pulling the inner tube into the outer tube to remove the rubber ring from the inner tube.

6 Claims, 8 Drawing Figures

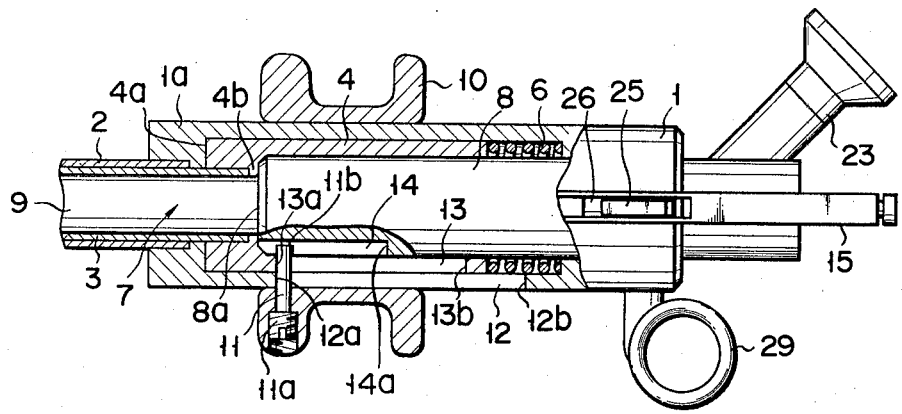
FIG. 1
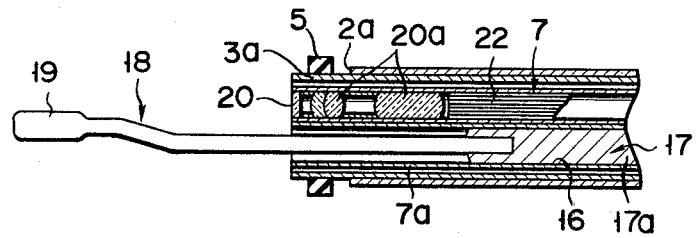
FIG. 2
FIG. 3
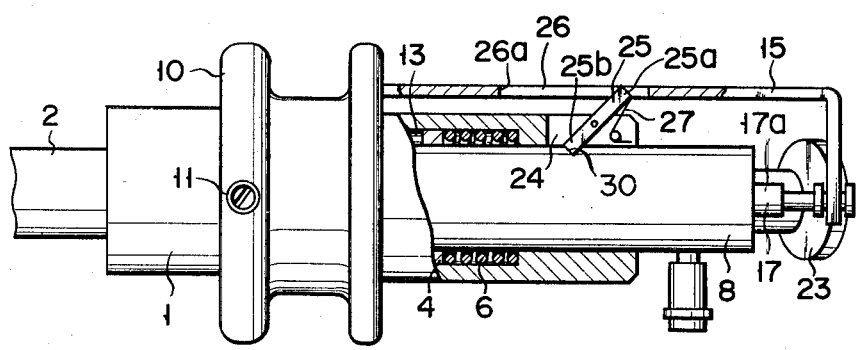
FIG. 4

RING APPLICATOR WITH AN ENDOSCOPE

BACKGROUND OF THE INVENTION

This invention relates to a ring applicator with an endoscope incorporated in it.

Known ring applicators have no means for observing the interior of a body cavity. It is therefore necessary to insert such a ring applicator into an extremely thick channel of an endoscope or to cut tissue layers or the wall of the living body to make an opening and insert an endoscope through the opening, thereby to observe the interior of a body cavity. To avoid these relatively intricate operations, an endoscope may be incorporated into the ring applicator. If this measure is adopted, however, the ring applicator will have too large a diameter or will become difficult to operate.

SUMMARY OF THE INVENTION

It is an object of this invention to provide a ring applicator with an endoscope, which is simple in construction, easy to operate and has a thinner outer diameter than known ring applicators.

According to this invention there is provided a ring applicator with an endoscope, which comprises an operation unit, an outer tube secured at one end coaxially to one end of the operation unit, an inner tube reciprocably inserted into the outer tube and having one end alternatively coming out of, and retreating into, the other end of the outer tube, a rubber ring removably mounted on the outer periphery of said one end of the inner tube, an endoscope reciprocably inserted into the inner tube, an operation device mounted on the operation unit, which, when moved toward the other end of the operation unit, moves the endoscope through the inner tube toward the other end of the operation unit and then moves both the endoscope and the inner tube toward the other end of the operation unit until the outer tube pushes and removes the rubber ring from the inner tube, a channel extending through the endoscope, and a forceps reciprocatively inserted into the channel and having a holding section protruding from the distal end of the endoscope.

BRIEF DESCRIPTION OF THE DRAWING

This invention can be fully understood from the following description with reference to the accompanying drawings in which:

FIG. 1 is a longitudinal sectional view of the proximal end portion of a ring applicator according to this invention;

FIG. 2 is a longitudinal sectional view of the distal end portion of the ring applicator shown in FIG. 1;

FIG. 3 is a front view of the distal end portion of the ring applicator shown in FIG. 2;

FIG. 4 is a partially broken plan view of the proximal end of the ring applicator shown in FIG. 1;

DESCRIPTION OF THE PREFERRED EMBODIMENT

Figure 5:
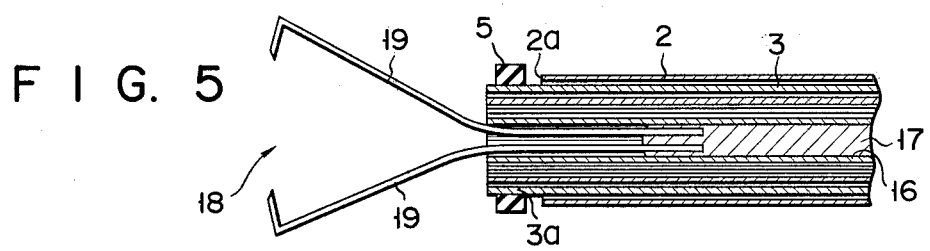
FIG. 5 is a longitudinal sectional view of the distal end portion of the ring applicator shown in FIG. 2, showing a pair of forceps strips opened most widely and protruding for the longest distance.

As shown in FIG. 1, a ring applicator of this invention comprises a hollow cylindrical operation unit 1, an outer tube 2 having its proximal end secured coaxially to the distal end of the operation unit 1, and an inner tube 3 reciprocably inserted into the outer tube 2. The inner tube 3 has its proximal end connected to a hollow cylindrical inner slider 4 which is reciprocatively movable in the operation unit 1. The inner tube 3 and the slider 4 can therefore move jointly. The slider 4 is always biased leftwards by means of a coil spring 6 which is disposed in the operation unit 1. In the leftmost position, the distal end 4a of the slider 4 contacts an inwardly projecting flange 1a integrally formed on the distal end of the operation unit 1. When the slider 4 is in the leftmost position, the distal end 3a of the inner tube 3 protrudes for a predetermined distance from a distal end 2a of the outer tube 2. A rubber ring 5 for clamping a tubular organ such as an oviduct is mounted on the periphery of the distal end 3a protruding from the outer tube 2, as shown in FIG. 2. Normally, the slider 4 stays in the leftmost position as shown in FIG. 1.

The ring applicator includes an endoscope 7. The endoscope 7 comprises a hollow cylindrical proximal end portion 8 and a tubular distal end portion 9 having a smaller outer diameter than the proximal end portion 8. The proximal end portion 8 is reciprocably inserted into the slider 4. The distal end portion 9 is inserted partly in the slider 4 and mostly in the inner tube 3. Further, a ring-shaped operation slider 10 is slidably mounted on the outer periphery of the operation unit 1.

The operation unit 1 has an elongated hole 12 extending lengthwise thereof. Similarly, the slider 4 has an elongated hole 13 extending in its lengthwise direction. The distal end 12a of the hole 12 is aligned with the distal end 13a of the hole 13. The proximal end 12b is nearer to the proximal end of the applicator than the proximal end 13b of the hole 13. An elongated groove 14 is formed in the outer periphery of the proximal end portion 8 and extends in the lengthwise direction of the proximal end portion 8. The groove 14 has its distal end opened at the distal end of the proximal end portion 8 and its proximal end 14a positioned nearer to the distal end of the proximal end portion 8 than the proximal end 13b of the elongated hole 13.

A connection pin 11 penetrates the elongated holes 12 and 13. Its outer end 11a makes a screw engagement with a female screw formed in the distal end portion of the operation slider 10.

The endoscope 7 is designed such that a pair of strips forming a holding section of a later described forceps 17 open when the proximal end portion 8 contacts a shoulder 4b disposed nearer to the distal end 4a of the slider 4 (FIG. 4). The forceps 17 is reciprocatively inserted into a forceps channel 16 which extends through the endoscope 7 as shown in FIGS. 2, 3 and 5 to 8.

Referring to FIG. 4, the forceps 17 is of open type and comprises a rod section 17a and a holding section 18. The rod section 17a is reciprocatingly inserted into the forceps channel 16 and protrudes at its proximal end from the proximal end of the operation unit 1. An L- shaped operation bar member 15 is connected at its proximal end to the protruded proximal end of the rod section 17a and at its distal end to the operation unit 1 so as to cause the slider 10 and the forceps 17 to move together back and forth. The holding section 18 comprises a pair of a hook-shaped strips 19 which are connected at their rear ends to the distal end of the rod section 17a and elastically biased away from each other in the outwardly radial direction of the rod section 17a. When the forceps 17 is moved toward the distal end 3a of the inner tube 3, the holding section 18 opens. When the forceps 17 is moved in the opposite direction, the holding section 18 closes as it is withdrawn into the channel 16.

In the endoscope 7, an observation light quide 22 extends parallel to the forceps channel 16. Between the distal end of the light guide 22 and an observation window 20 provided at the distal end of the endoscope 7, there are arranged observation lenses 20a. Thus, the light guide 22 is optically connected to the observation window 20 through the lenses 20a. The proximal end of the light guide 22 is optically connected to an ocular portion 23 provided at the proximal end of the endoscope 7.

As shown in FIG. 3, an illumination window 21 is provided at the distal end of the endoscope 7. The window 21 occupies the whole distal end area of the endoscope 7 except for the area occupied by the holding section 18 and the observation window 20. The illumination window 2 is optically connected to an illumination light guide (not shown) which extends through the endoscope 7. The proximal end of the illumination light guide is connected to, as in the known endoscope, a bundle of optical fibers (not shown) which is outside of the endoscope 7 and is connected to a light source (not shown). The light from the light source is transmitted through the illumination light guide and is emitted from the illumination window 21 thereby to illuminate an object, e.g. an oviduct. The light reflected from the object is received by the observation window 20 and guided through the observation lenses 20a and the observation light guide 22. The object can therefore be observed at the ocular portion 23.

As shown in FIG. 4, a slit 24 is formed in the outer periphery of the proximal end portion of the operation unit 1 and is positioned so as to face the operation bar member 15. In the slit 24 a stop pin 25 is swingably supported at its central portion. The stop pin 25 is biased counterclockwise by a torsion spring 27 so that its one end 25a protrudes from the operation unit 1 and its other end 25 normally engages a recess 30 formed in the outer periphery of the proximal end portion 8 of the endoscope 7. The operation bar member 15 has an elongated hole 26 which faces the slit 24 and thus the stop pin 25. Normally, said one end 25a of the stop pin 25 is disposed in the elongated hole 26. When the operation bar member 15 is moved backward together with the operation slider 10 for a predetermined distance, the distal end 26a of the hole 26 hits said one end 25a of the stop pin 25 and then rocks the pin 25 clockwise against the torsion spring 27, thus releasing said other end 25b of the pin 25 from the recess 30.

A ring 29 may be attached to the proximal end of the operation unit 1 as shown in FIG. 1. The operator inserts his finger into or applies the finger to the ring 29 thereby to operate the applicator easily.

Now it will be described how to operate the ring applicator of the above-mentioned construction.

First, the operation slider 10 is pulled toward the proximal end of the operation unit 1 until the pin 11 contacts the proximal end 14a of the elongated groove 14. The forceps 17, which is connected to the slider 10 by means of the operation rod 15, is also pulled toward the proximal end of the operation unit 1. As a result, the strips 19 are pulled into the forceps channel 16, and the holding section 18 closes. Then, the outer tube 2 and inner tube 3 of the ring applicator is inserted into a body cavity through a trocar or an insertion channel of another endoscope. This done, the operation slider 10 is pushed toward the distal end of the operation unit 1, thereby pushing the holding section 18 out of the forward end of the forceps channel 16 to open the member 18 as shown in FIG. 5. While observing the interior of the body cavity through the endoscope 7 in the applicator, the operator moves the applicator farther into the body cavity until an oviduct 28 is disposed between the strips 19. The operation slider 10 is pulled again toward the proximal end of the operation unit 1, thus pulling the forceps 17 into the forceps channel 16. The holding section 18 therefore closes and firmly holds the oviduct 28 as shown in FIG. 6.

As long as the pin 11 moves in the range of the elongated groove 14, the operation slider 10 and the forceps 17 is displaced in the same direction as that of the pin 11 without moving the endoscope 7. Thus, it can be easily observed how the forceps 17 moves and operates in the body cavity. The stop pin 25 whose other end, engages the recess 26 of the proximal end portion 8 prevents the endoscope 7 from moving toward the proximal end of the operation unit 1. Even if the stop pin 25 is not provided, the endoscope 7 can not so easily move backward under the normal condition. Thus, the stop pin 25 guarantees a safe operation of the ring applicator.

Figure 6:
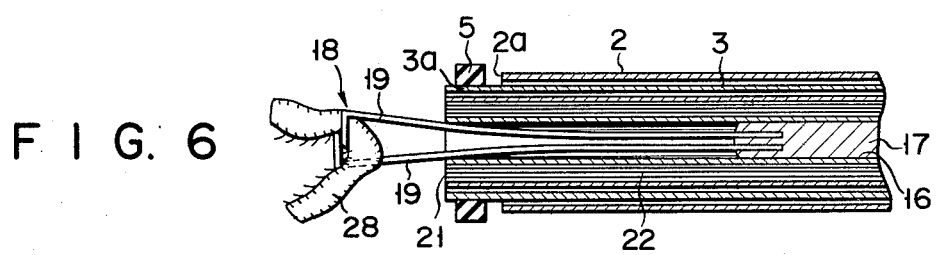
FIG. 6 is a longitudinal sectional view of the distal end portion of the ring applicator shown in FIG. 2, showing a pair of forceps strips holding an oviduct.
Figure 7:
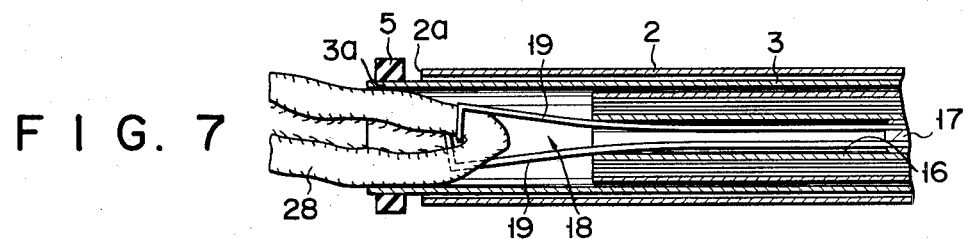
FIG. 7 is a longitudinal sectional view of the distal end portion of the ring applicator shown in FIG. 2, showing a pair of forceps strips drawing an oviduct into the inner tube of the applicator.

As the forceps 17 firmly holding the oviduct 28 as shown in FIG. 6 is pulled farther into the channel 16, the distal end 26a of the elongated hole 26 of the operation bar member 15 hits said one end 25a of the stop pin 25 and pushes it. Thus, the stop pin 25 rocks clockwise against the torsion spring 27, thereby releasing the other end 25b of the pin 25 from the recess 26. As the operation slider 10 is further pulled backward, the pin 11 contacts the proximal end 14a of the elongated groove 14 of the endoscope 7. When the operation slider 10 is further pulled backward, the endoscope 7 is moved backward together with the operation slider 10 and the forceps 17. As a result, the oviduct 28 is pulled into the inner tube 3 as shown in FIG. 7.

Figure 8:
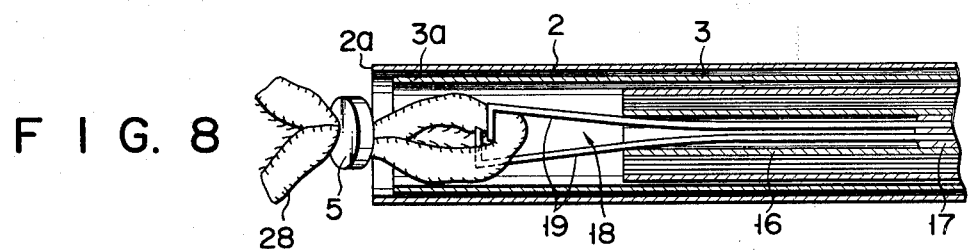
FIG. 8 is a longitudinal sectional view of the distal end portion of the ring applicator shown in FIG. 2, showing a rubber ring clamping an oviduct.

As the operation slider 10 is still further pulled toward the proximal end of the operation unit 1, the pin 11 contacts the proximal end 13b of the elongated hole 13 of the slider 4. When the slider 10 is pulled rearward further, the inner tube 3 together with the slider 4 is moved backward together with the operation slider 10, the forceps 17 and the endoscope 7. In this way, the inner tube 3 is pulled into the outer tube 2. Then, the rubber ring 5 mounted on the outer periphery of the distal end portion of the inner tube 3 is pushed by the distal end 2a of the outer tube 2 to be released from the inner tube 3 thereby to clamp the oviduct 28 as shown in FIG. 8.

Thereafter, the operation slider 10 is pushed toward the distal end of the operation unit 1 until the inner tube 3 and the forceps 17 are moved to such positions as shown in FIG. 5. The holding section 18 therefore opens, thus releasing the oviduct 28 in such a manner that the oviduct 28 is clamped by the rubber ring 5.

Then, the operation slider 10 is pulled toward the proximal end of the operation unit 1 until the holding section 18 of the forceps 17 is withdrawn into the inner tube 3. After this the distal end portion of the ring applicator is pulled out of the body cavity, thus completing ring application.

A mentioned above, the operation slider 10 is moved back and forth with respect to the operation unit 1, thereby causing the forceps 17 to hold an oviduct 28 and allowing the rubber ring 5 to clamp the oviduct 28. In other words, a single member serves to achieve two operations. In addition, these operations are carried out, while the interior of the body cavity is observed by the endoscope 9 in the applicator. The ring application can therefore be carried out safely and quickly. Since another endoscope is unnecessary, it is of course unnecessary to cut the wall of a living body, through which the endoscope is to be inserted into a body cavity. Moreover, the forceps 17 can be opened and closed without moving the endoscope 7. That is, the forceps 17 can be operated independently of the endoscope 7. The distal end of the endoscope 7 would not be withdrawn into the inner tube 3 while the forceps 17 is operated, whereby the interior of the body cavity is observed without interruption.

What is claimed is:

1. A ring applicator comprising:
   an operation unit having one end and another end opposite to said one end;
   an outer tube coaxially arranged with the operation unit and having one end thereof connected to said one end of the operation unit and the other end thereof open;
   an inner tube reciprocatingly inserted into the outer tube and having one end protruding from and drawn into the outer tube at said other end of the outer tube and the other end open;
   a rubber ring removably mounted on an outer periphery of said one end of the inner tube;
   an endoscope comprising a proximal end portion and a distal end portion fixed thereto and having a channel extending therethrough and reciprocatingly inserted into the inner tube, said channels having one end adjacent to said one end of the inner tube;
   a forceps reciprocatingly inserted into the channel in the endoscope and adapted to be opened when the forces protrudes from said one end of the channel; and
   an operation device reciprocatingly mounted on the operation unit and including means to pull at first only the forceps into the channel of the endoscope for a predetermined length to close the forceps, then move the endoscope as well as the forceps toward the operation unit relative to the inner tube to draw the forceps into the inner tube and thereafter move the inner tube as well as the endoscope toward the operation unit relative to the outer tube for allowing said other end of the outer tube to push the rubber ring for removal of the rubber ring from the inner tube, as the operation device is being moved toward said other end of the operation unit.

2. The ring applicator according to claim 1, wherein said forceps comprises a rod section reciprocatively inserted into said channel and having one end protruding from said other end of operation unit and a pair of hook-shaped strips sectured at proximal ends to the other end of the rod section and biased normally away from each other in a diametrical direction of the rod section.

3. The ring applicator according to claim 2, wherein said operation device comprises:
   a hollow cylindrical operation slider surrounding said operation unit and slidable along the operation unit;
   a first elongated hole formed in an outer periphery of the operation unit and extending along the operation unit;
   a hollow cylindrical inner slider surrounding the proximal end portion of said endoscope, slidable along the endoscope, inserted in said operation unit and movable reciprocatively along the operation unit, biased normally toward said one end of the operation unit, and connected at one end to said other end of the inner tube;
   a second elongated hole formed in an outer periphery of the inner slider, extending lengthwise of the inner slider, and entirely opening to the first elongated hole;
   an elongated groove formed in an outer periphery of the proximal end portion of the endoscope and positioned near said one end of the operation unit for regitration with the second elongated hole;
   a connection pin penetrating the first and second elongated holes, secured at one end to the operation slider and diposed at the other end in the elongated groove; and
   an operation bar member connected at one end to the operation slider and at the other end to said one end of the proximal end portion of the forceps.

4. The ring applicator according to claim 3, wherein ends of the first elongated hole, the second elongated hole and the elongated groove which are disposed nearer to said other end of the operation unit are so arranged that, as the operation device is moved toward said other end of the operation unit, the forceps strips are drawn into the endoscope to be closed until the connection pin abuts against said end of the elongated groove, the endoscope is drawn into the inner tube until the connection pin abuts against said end of the second elongated hole, and then the inner tube is moved toward said other end of the operation unit with respect to the outer tube until the connection pin abuts against said end of the first elongated hole to allow the rubber ring to be removed from the endoscope is pulled into said inner tube, and when said rubber ring is removed by the outer tube from the inner tube, respectively.

5. The ring applicator according to claim 4, wherein stop means is provided between the operation bar member and the outer periphery of the proximal end portion of said endoscope.

6. The ring applicator according to claim 4, wherein said stop means comprises:
   a recess formed in an outer periphery of the proximal end portion of the endoscope;
   a stop pin rockably supported at said other end of the operation unit having one end and the other end opposite thereto;
   a spring provided at said other end of the operating unit for normally urging the stop pin to allow said one end of the stop pin to engage the recess; and
   an elongated hole formed in the operation bar member, extending lengthwise thereof to normally allow the other end of the stop pin to be disposed therein and having a distal end abutting against said other end of the stop pin for rotating the stop pin to disengage said one end of the stop pin from the recess when the operation slider is moved toward said other end of the operation unit.

* * * * *